United States Patent
McCary

(10) Patent No.: US 8,393,898 B2
(45) Date of Patent: Mar. 12, 2013

(54) APPARATUS FOR FILTERING DENTAL SOLID WASTE

(76) Inventor: Charles McCary, Huntsville, AL (US)

(*) Notice: Subject to any disclaimer, the term of this patent is extended or adjusted under 35 U.S.C. 154(b) by 1238 days.

(21) Appl. No.: 12/136,151

(22) Filed: Jun. 10, 2008

(65) Prior Publication Data

US 2008/0257815 A1  Oct. 23, 2008

Related U.S. Application Data

(63) Continuation-in-part of application No. 11/111,618, filed on Apr. 21, 2005, now abandoned.

(51) Int. Cl.
A61C 17/06 (2006.01)

(52) U.S. Cl. ............ 433/92; 433/91; 433/95; 210/446; 210/448; 604/541

(58) Field of Classification Search ............ 433/92, 433/91, 95; 604/541
See application file for complete search history.

(56) References Cited

U.S. PATENT DOCUMENTS

| | | | |
|---|---|---|---|
| 3,051,175 A | 8/1962 | Nugent | |
| 3,476,144 A * | 11/1969 | Krantz | 433/92 |
| 3,890,712 A * | 6/1975 | Lopez | 433/92 |
| 4,097,381 A | 6/1978 | Ritzler | |
| 5,577,910 A | 11/1996 | Holland | |
| 5,667,382 A | 9/1997 | Holland | |
| 5,741,134 A * | 4/1998 | Davis | 433/91 |
| 5,741,397 A | 4/1998 | Kraver | |
| 5,766,134 A * | 6/1998 | Lisak et al. | 600/562 |
| 5,797,742 A | 8/1998 | Fraker | |
| 6,299,444 B1 | 10/2001 | Cohen | |
| 6,299,763 B1 * | 10/2001 | Ashman | 210/94 |
| 6,409,803 B1 | 6/2002 | Tremel et al. | |
| 6,592,769 B1 | 7/2003 | Erickson | |
| 6,790,038 B2 | 9/2004 | Hubner et al. | |
| 7,182,599 B2 | 2/2007 | Stone et al. | |
| 7,306,460 B2 | 12/2007 | Hubner et al. | |
| 7,631,758 B2 | 12/2009 | Stennes et al. | |
| 2004/0222141 A1 | 11/2004 | Gray | |
| 2005/0239016 A1 | 10/2005 | McCary | |
| 2006/0093990 A1 | 5/2006 | Stone et al. | |
| 2008/0099390 A1 | 5/2008 | Plath | |
| 2008/0257759 A1 | 10/2008 | Stone et al. | |
| 2008/0257815 A1 | 10/2008 | McCary | |

FOREIGN PATENT DOCUMENTS

DE  3423836  6/1987

* cited by examiner

*Primary Examiner* — Duane Smith
*Assistant Examiner* — Paul J Durand
(74) *Attorney, Agent, or Firm* — Jeremy A. Smith; David M. Mixon; Bradley Arant Boult Cummings LLP

(57) ABSTRACT

An apparatus for filtering dental solid waste has been developed. The apparatus includes a high volume evacuation (HVE) tip with one end that is connected to a suction line and another end that is inserted in a patient's mouth to remove dental waste. A filtration unit is located within the HVE tip that retains solid dental waste within the HVE tip.

6 Claims, 8 Drawing Sheets

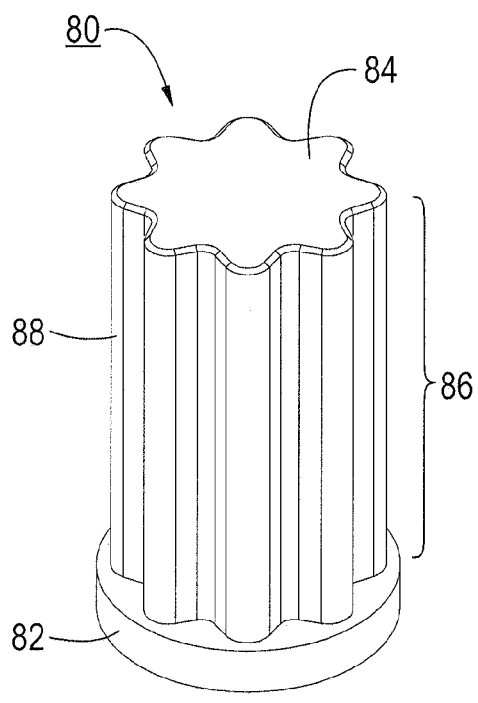
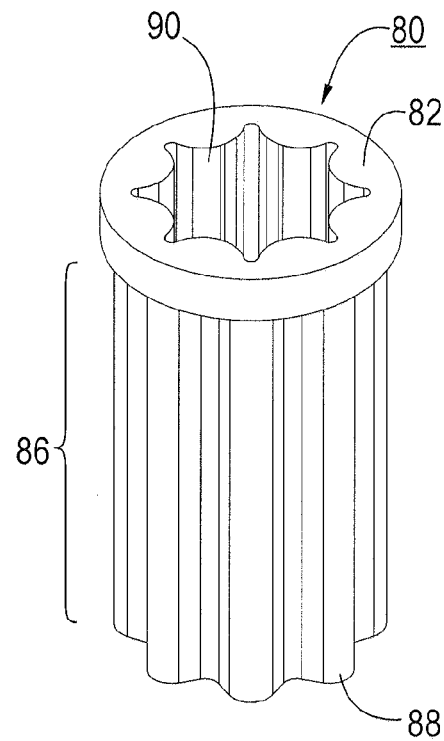
FIG. 8A  FIG. 8B
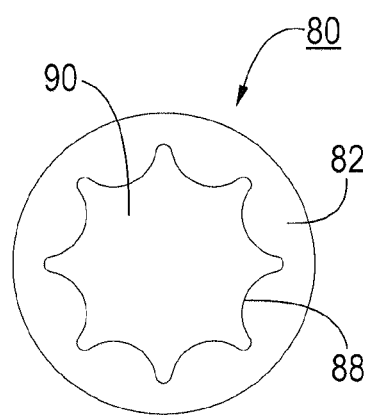
FIG. 8C

_US 8,393,898 B2_

APPARATUS FOR FILTERING DENTAL SOLID WASTE

CROSS-REFERENCE TO RELATED APPLICATIONS

This application is a continuation-in-part of application Ser. No. 11/111,618, filed Apr. 21, 2005 entitled "Apparatus for Filtering Dental Solid Waste", which claimed priority from U.S. Provisional Application 60/564,334 entitled "Apparatus for Filtering Dental Solid Waste" that was filed on Apr. 22, 2004.

BACKGROUND OF INVENTION

1. Field of the Invention

The invention relates generally to medical devices. More specifically, the invention relates to an apparatus for filtering dental solid waste.

2. Background Art

When filings in teeth are replaced or removed, the composition of the filings is often a mixture of such materials as silver, mercury, copper, zinc, tin, palladium, etc. These materials, along with other solid or semi-solid debris, pose disposal problems for dental facilities since they may contain hazardous and possibly bio-hazardous material.

Such material is typically removed from the patient's mouth by a high volume evacuation (HVE) tip as shown in FIG. 1. The HVE tip 10 is attached to a tube 12 with a vacuum that draws both liquid and solid material from the patient's mouth. A first filtration canister 14 is located at the patient's chair to provide an initial filtration to remove solid debris. A second filtration trap 16 is located further along the line before the vacuum pump 18. After the vacuum pump, the filtered liquid in disposed in the sewer.

The filtration canister and the filtration trap are each periodically cleaned by hand. This typically involves removed the filtration screen from the canister or trap and cleaning off the filtered debris. This is an unpleasant, messy and potentially dangerous process since the person responsible for the cleaning is exposed to these materials. Additionally, the filtered materials such as mercury must be disposed of properly since they cannot simply be added to the sewer or trash.

SUMMARY OF INVENTION

In some aspects, the invention relates to an apparatus for filtering dental solid waste, comprising: a high volume evacuation (HVE) tip with a first end that is connected to a suction line and a second end that is inserted in a patient's mouth to remove dental waste; and a filtration unit that is located between the first end of the HVE tip and the second end of the HVE tip, where the filtration unit retains solid dental waste within the HVE tip.

In other aspects, the invention relates to an apparatus for filtering dental solid waste, comprising: a high volume evacuation (HVE) tip with a first end that is connected to a suction line and a second end that is inserted in a patient's mouth to remove dental waste; and means for filtering and retaining dental solid waste within the HVE tip.

Other aspects and advantages of the invention will be apparent from the following description and the appended claims.

BRIEF DESCRIPTION OF DRAWINGS

It should be noted that identical features in different drawings are shown with the same reference numeral.

FIGS. 8a-8c show perspective and cross-sectional views of the cylindrically shaped filter assembly in accordance with one embodiment of the present invention.

DETAILED DESCRIPTION

Figure 1:
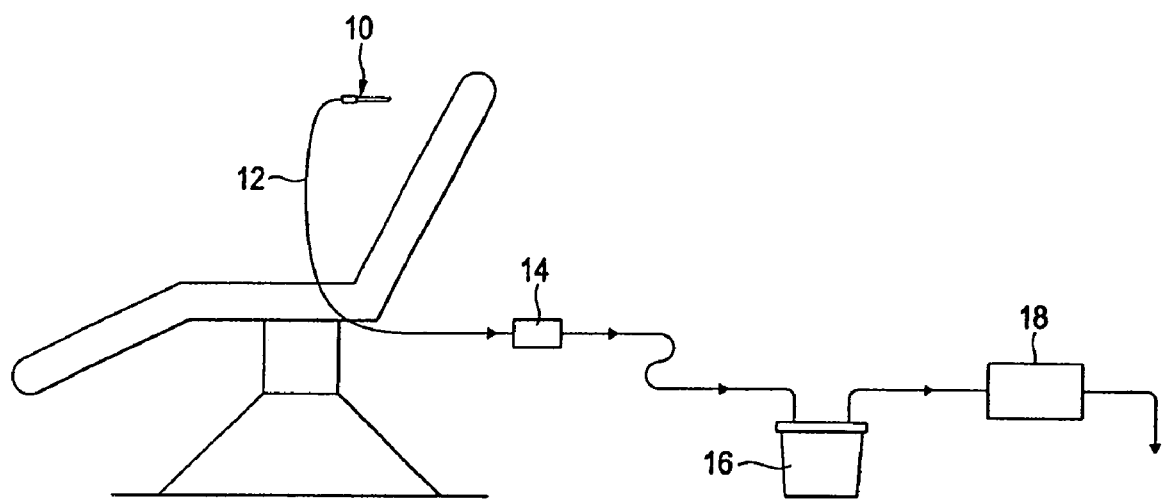
FIG. 1 shows a diagram of a prior art filtration system for dental solid waste.
Figure 2A:
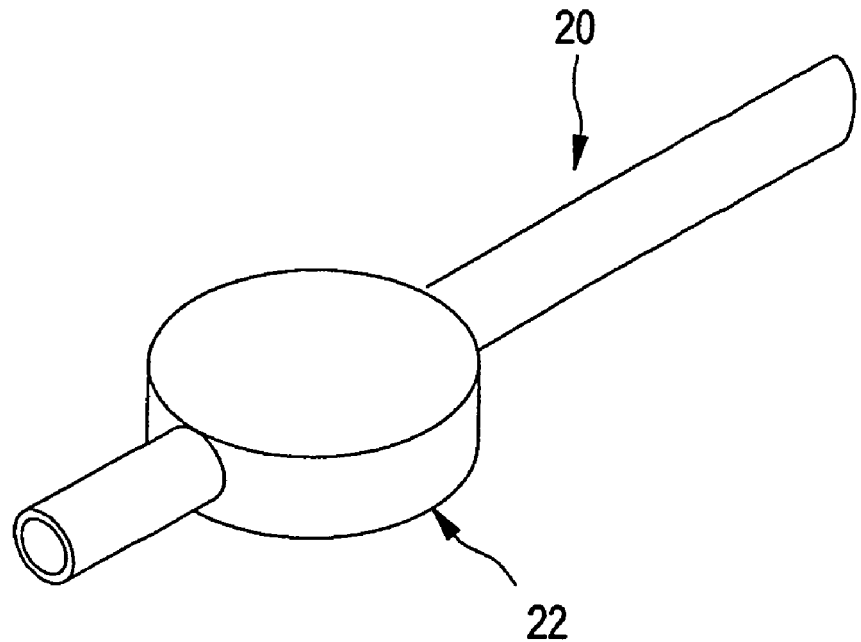
FIGS. 2a and 2b show perspective views of a High Volume Evacuation (HVE) tip both with and without a Saliva Ejector (SE) in accordance with one embodiment of the present invention.
Figure 2B:
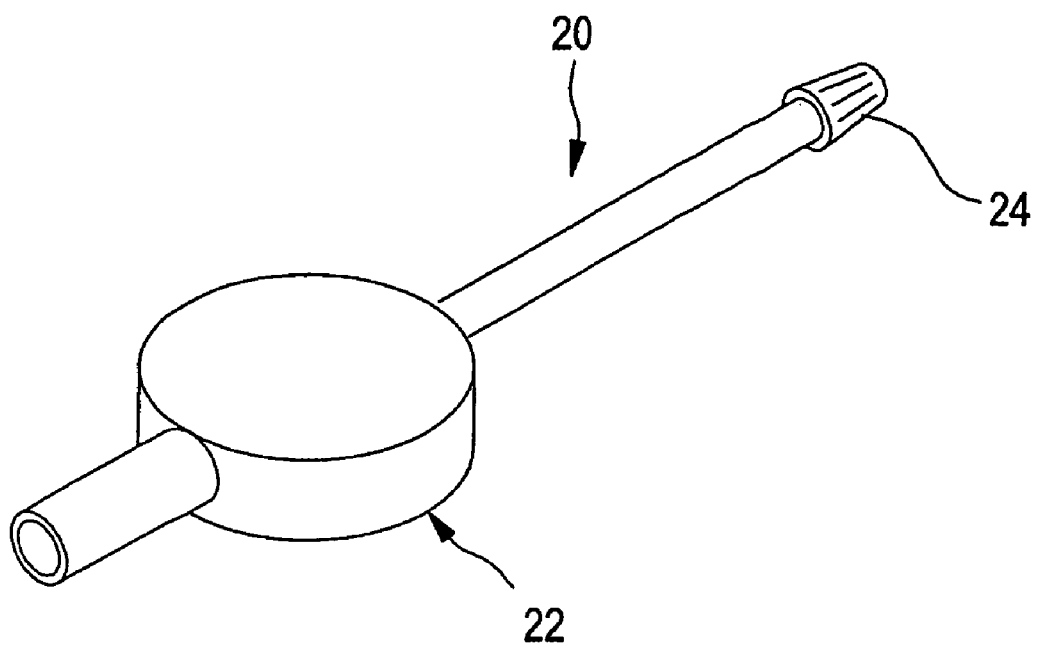

An apparatus to filter dental solid waste has been developed. FIGS. 2a and 2b shows perspective views of a High Volume Evacuation (HVE) tip 20 both with and without a Saliva Ejector (SE) 24 in accordance with one embodiment of the present invention. The tip of the HVE 20 has a filter 22 container that is integral to the body. The tip is then connected to the tube attached to the vacuum pump (not shown in FIG. 2). The device also is shown in FIG. 2a with a SE tip 24 that is optionally attached on the end. Typically, a new tip is used for each patient. This allows the tip with the container to be removed from the line after the procedure is completed. The used tip is then easily, cleanly, and safely disposed of in an appropriate manner.

Figure 3A:
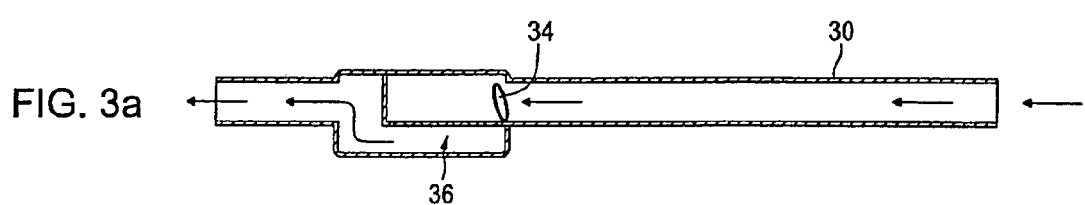
FIGS. 3a-3c show top and cross-sectional views of a High Volume Evacuation (HVE) tip both with and without a Saliva Ejector (SE) in accordance with one embodiment of the present invention.
Figure 3B:
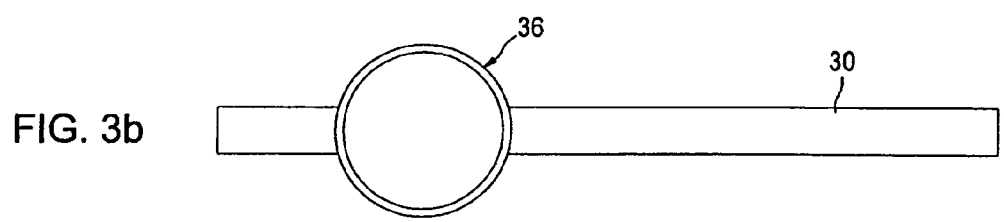
Figure 3C:
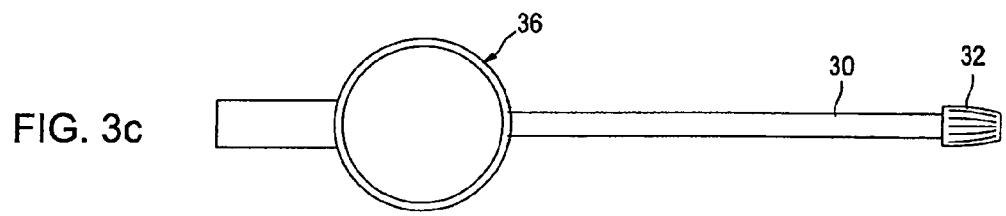

FIGS. 3a-3c show top and cross-sectional views of a High Volume Evacuation (HVE) tip 30 both with and without a Saliva Ejector (SE) 32 in accordance with one embodiment of the present invention. In this alternative embodiment, a flip valve or check valve 34 is include in the filter container 36 to prevent any backflow of filtered debris from returning to the patient's mouth.

Figure 4:
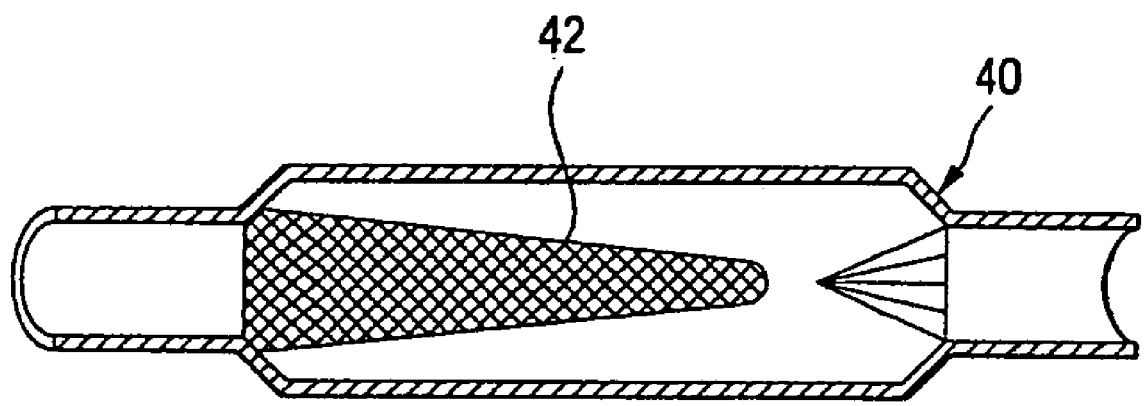
FIG. 4 shows a cross-sectional view of a High Volume Evacuation (HVE) tip in accordance with an alternative embodiment of the present invention.
Figure 5A:
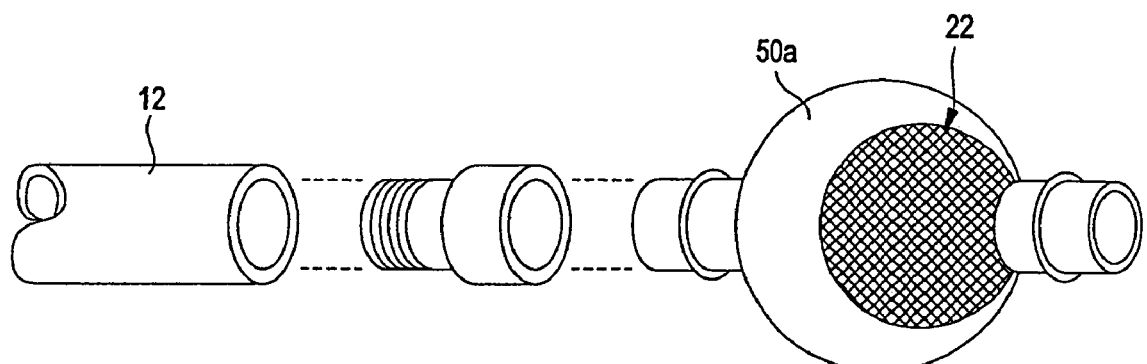
FIGS. 5a and 5b show cross-sectional views of a High Volume Evacuation (HVE) tip in accordance with other alternative embodiments of the present invention.
Figure 5B:
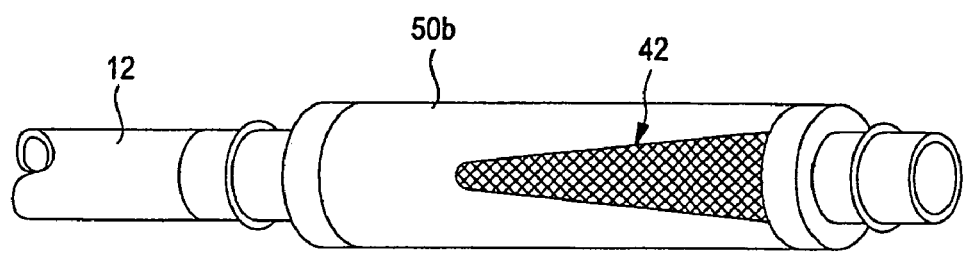

FIGS. 4 and 5 show views of other alternative embodiments of the present invention. FIG. 4 shows a cross sectional view a disposable HVE tip 40 with a conical shaped filter 42 that provides greater surface area for the filter. In other embodiments, the filter container may be a detachable cartridge that is removed from the tip for separate disposal. FIGS. 5a and 5b show cross sectional views of an example of detachable HVE filtration cartridges 50a and 50b.

Figures 6A, 6B, 6C:
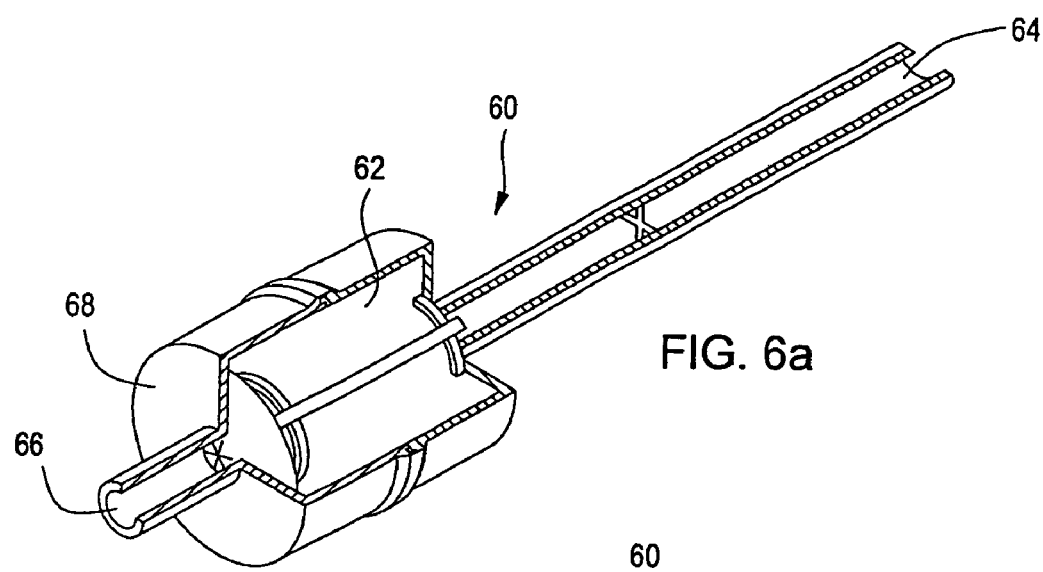
FIGS. 6a-6c show cut-away views of a High Volume Evacuation (HVE) tip in accordance with other alternative embodiments of the present invention.

FIGS. 6a-6c show cut-away views of a High Volume Evacuation (HVE) tip 60 in accordance with other alternative embodiments of the present invention. In this embodiment, the filter 62 is completely contained within a disposable HVE tip 60. The suction end 64 of the tip is inserted into the patient's mouth. A saliva ejector (not shown) may be included if desired. The other end 66 of the tip is connected to the vacuum line (not shown) that provides suction for the invention. The filter 62 is entirely contained within the filter housing 68.

This embodiment of the invention is a disposable HVE tip with integrated filter. It is intended to be disposed after a single use. The HVE tip may include a check value to ensure retention of the dental waste within the device. The device is also flexible in the design of filters to be used. In some embodiments, the housing 68 may be opened to change a filter if needed. Other embodiments may use a sealed housing to prevent possible spillage of the filtered waste.

A conical shaped filter (as shown previously) or other suitable design may be inserted in the filter housing. However, any other suitable filter design may be used in any of the embodiments previously discussed. In some examples, the filter used in the invention should be able to capture debris greater than 30 microns in size. However, filters of different size may be used. If a filter designed to capture smaller debris (e.g., 10 microns and larger), the HVE tip may begin to lose effectiveness due to debris clogging the filter and resulting in a loss of suction. Features such as circular ridging, may be placed in the interior of the HVE tip before the filter to create a centrifugal action on the debris flow in order to dislodge any debris that gets stuck. Other features may be included to increase the effectiveness of the suction line be adding an "air venturi" to the HVE tip.

In contrast to previous statements, the filtration unit, in an alternative embodiment, is permanently sealed to allow the dental solid waste to be disposed of in a safe and environmentally friendly manner by reducing the chance of accidental exposure to the dental solid waste. In this embodiment, the permanently sealed filtration unit protects both the individual tasked with changing and/or disposing of the filtration unit as well as the environment. The permanently sealed filtration unit keeps the hazardous solid dental waste from contacting the individual or being released into the environment.

Figure 7A:
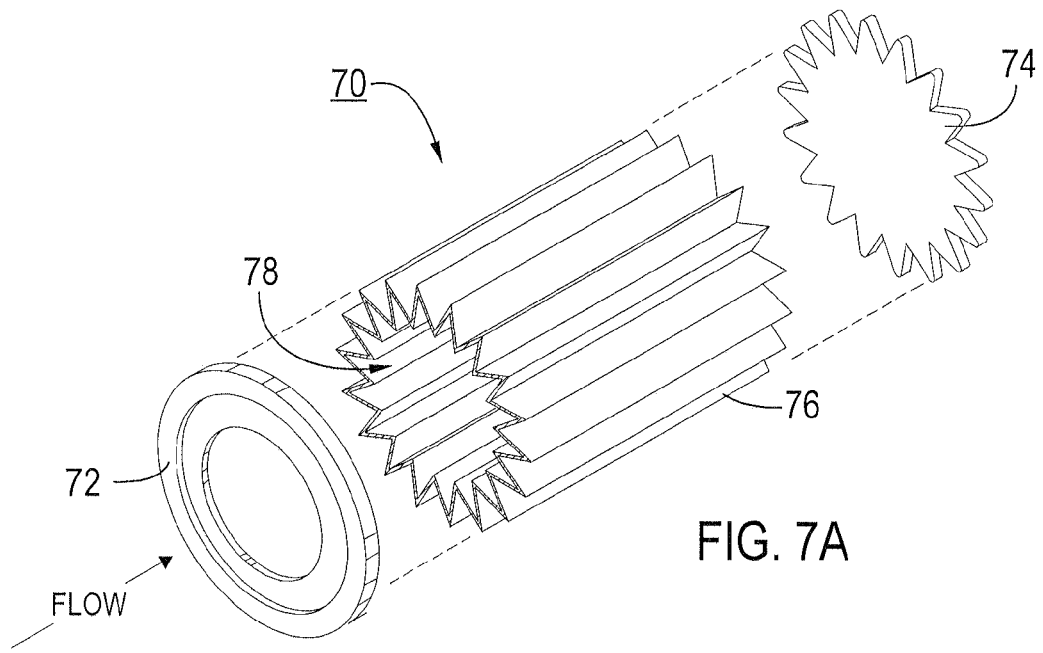
FIGS. 7a-7c show perspective and cross-sectional views of the cylindrically shaped filter assembly in accordance with one embodiment of the present invention.
Figure 7B:
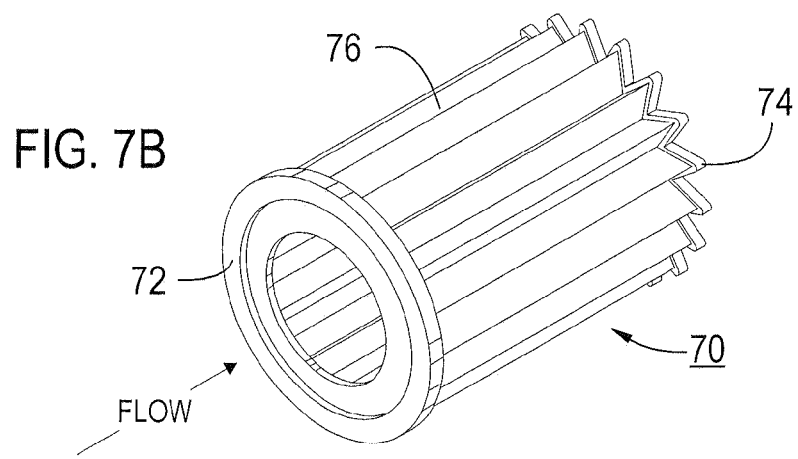
Figure 7C:
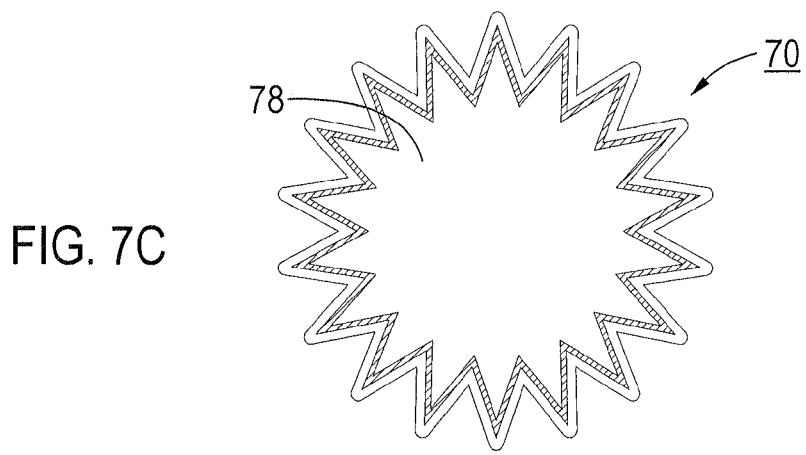

Another embodiment of the filtration unit is shown in FIGS. 7a-c. Generally, the filtration unit includes a filter assembly 70, inlet cap 72, a hollow portion 78 and an end cap 74. The filter assembly 70 has a plurality of folded pleats 76 to increase the surface area and efficiency of the filtration unit. In one embodiment, the filter assembly 70 contains eighteen (18) folded pleats 76 with equal surface area per section. In this embodiment, the filter assembly 70 may be made from UPS Class I materials, although any other filtration material approved for dental use is contemplated. In this embodiment the inlet cap 72 and end cap 74 may be made of ABS plastic. In this embodiment, the filter assembly 70 is designed to trap or "filter" solid dental waste greater than 10 microns.

FIGS. 8a-8c show yet another embodiment of the filtration unit, in this embodiment the filtration unit 80 may be manufactured from one piece of USP Class 1 or ABS class 1 material (i.e., a single composition), although any other filtration material approved for dental use is contemplated. The filtration unit 80 includes a filter assembly 86, inlet cap 82, a hollow portion 90 and an end cap 84 all manufactured from a single piece of material. The filter assembly 86 has a plurality of folded pleats 88 to increase the surface area and efficiency of the filtration unit 80. In one embodiment, the filter assembly 86 contains eighteen (18) folded pleats 88 with equal surface area per section. In another embodiment, the filter assembly 86 contains eight (8) folded pleats 88 with equal surface area per section.

Notwithstanding previous statements, subsequent experimental results for this embodiment have shown that a filter assembly with a 10 micron pore size (i.e., retains solid dental waste larger than 10 microns) will function properly in the present invention. It is believed that the increased filter surface area achieved by including folded pleats (as shown in FIGS. 7a-7c) in the filter assembly allow for the smaller pore size. Accordingly, one embodiment of the present invention incorporates a filter, which may be either conical or cylindrical, with a 10 micron pore size.

Now referencing FIGS. 6a-c, in yet another embodiment, the suction end 64 is designed to receive or connect to a 0.4375 (7/16) inch tip which is inserted into the patient's mouth. In this embodiment, the other end 66 of the tip is designed to receive or connect to a 0.500 (½) or 0.625 (5/8) inch vacuum line (not shown).

The present invention has the advantages of providing a disposable, self-contained HVE tip that catches solid dental waste. The waste is collected at the source so the chance of contamination in the waste system is minimized. Each HVE tip completely contains the waste so that the change of spillage is also minimized. Additionally, the tip may be easily disposed after a single use. Further, costs may be reduced by using a conventional HVE non-filtration tip when there is no chance of contamination from solid waste.

In summary, the advantages of the present invention include a self-contained filtration apparatus that is disposable and a filtration apparatus that minimizes contact with hazardous materials. While the invention has been described with respect to a limited number of embodiments, those skilled in the art, having benefit of this disclosure, will appreciate that other embodiments can be devised which do not depart from the scope of the invention as disclosed here. Accordingly, the scope of the invention should be limited only by the attached claims.

I claim:

1. An apparatus for filtering dental solid waste, comprising:
   a single-use disposable high volume evacuation (HVE) tip with a first end that connects to 0.500 (½) inch ID central vacuum tube and a second end that connects to a 0.4375 (7/16) inch tip that is inserted in a patient's mouth to remove dental waste;
   a filtration unit adapted to retain solid dental waste within the HVE tip located between the first end of the HVE tip and the second end of the HVE tip, where the filtration unit comprises an internal unitary conically shaped filter assembly positioned so that a flow of liquid through the internal filter assembly contacts the filter assembly at an acute angle, and a unitary filter housing which contains the conically shaped filter assembly,
   wherein the filtration unit is a unitary structure, as to prevent access to the internal conically shaped filter assembly by a user of the apparatus, and retains solid dental waste of a size greater than 10 microns; and
   a check valve located between the filtration unit and the second end of the HVE tip, where the check valve ensures retention of the solid dental waste within the HVE tip.

2. The apparatus of claim 1, where the first end of the HVE tip connects to 0.625 (5/8) inch ID central vacuum tubing.

3. An apparatus for filtering dental solid waste, comprising:
   a single-use disposable high volume evacuation (HVE) tip with a first end that is connected to a suction line and a second end that is inserted in a patient's mouth to remove dental waste; and a filtration unit adapted to retain solid dental waste within the HVE tip, the filtration unit being located between the first end of the HVE tip and the second end of the HVE tip, the filtration unit further comprising:

an internal unitary conically shaped filter assembly comprising a plurality of filter assembly boundaries, said filter assembly positioned so that the majority of a flow of liquid through the filter assembly contacts the filter assembly boundaries at an acute angle, and a unitary filter housing which contains the conically shaped filter assembly, wherein the filtration unit is a unitary structure as to prevent access to the filter assembly by a user of the apparatus.

4. The apparatus of claim 3, further comprising:

a check valve located between the filtration unit and the second end of the HVE tip, where the check value ensures retention of the solid dental waste within the HVE tip.

5. The apparatus of claim 3, where the filtration unit retains solid dental waste of a size greater than 30 microns.

6. The apparatus of claim 3, where the filtration unit retains solid dental waste of a size greater than 10 microns.

* * * * *